US00PP29312P3

(12) United States Plant Patent
van Langen

(10) Patent No.: US PP29,312 P3
(45) Date of Patent: May 22, 2018

(54) ***ECHEVERIA* PLANT NAMED 'AMIECH1604'**

(50) Latin Name: ***Echeveria* hybrid**
Varietal Denomination: AMIECH1604

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days. days.

(21) Appl. No.: 15/530,476

(22) Filed: Jan. 20, 2017

(65) Prior Publication Data

US 2018/0027719 P1 Jan. 25, 2018

(30) Foreign Application Priority Data

Jul. 25, 2016 (QZ) ..... PBR 2016/1798

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Echeveria* cultivar named 'AMIECH1604' which is characterized by a fast rate of growth, improved winter hardiness, and a flattened globular plant shape with thick, robust foliage with a broad obovate to spatulate shape which is arranged in a compact rosette. The juvenile foliage towards the center of the rosette exhibits a pink to red general coloration with pink margins, and mature foliage towards the outer whorls of the rosette that exhibits a red-purple general coloration with greyed-red margins. The new variety has shown to be uniform and stable in the resulting generations from asexual propagation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'AMIECH1604'.

BACKGROUND OF THE INVENTION

Parentage: 'AMIECH1604' is a spontaneous whole-plant mutation of *Echeveria* 'Perle Von Nürnberg' (not patented) which was discovered by the inventor in September of 2013 at a commercial greenhouse in Heerhugowaard, the Netherlands. The mutation was first noted for its thick, robust pink to red foliage by comparison to the thinner, weaker greyed-purple foliage of the parent plant. The mutation was isolated for further evaluation to confirm the stability of the characteristics initially observed. In the summer of 2014, the claimed plant was selected for commercialized.

Asexual Reproduction: Asexual reproduction of the new cultivar 'AMIECH1604', by way of rooting leaf cuttings, was first initiated in the summer of 2015 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH1604' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1604'. These characteristics in combination distinguish 'AMIECH1604' as a new and distinct *Echeveria* cultivar:

1. 'AMIECH1604' exhibits a fast growth rate and improved winter hardiness; and
2. 'AMIECH1604' exhibits thick, robust foliage with a slight upwardly curved attitude, arranged in a compact rosette; and
3. 'AMIECH1604' exhibits broad obovate to spatulate foliage with an apiculate apex; and
4. 'AMIECH1604' exhibits moderately pruinose foliage; and
5. 'AMIECH1604' exhibits juvenile foliage with a pink to red general coloration and pink margins, the colors becoming more intense with exposure to ultraviolet light; and
6. 'AMIECH1604' exhibits mature foliage with a red-purple general coloration and greyed-red margins, the colors becoming more intense with exposure to ultraviolet light.

BOTANICAL DESCRIPTION OF THE PLANT

Figure 1:
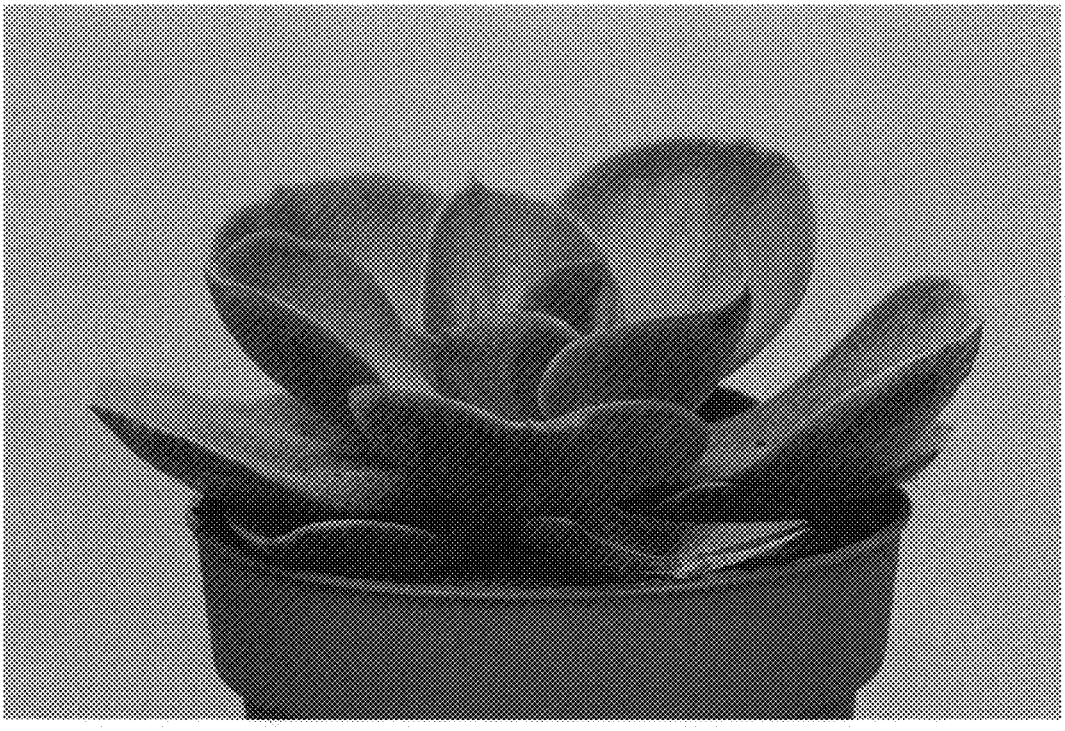
FIG. 1 illustrates, as nearly true as it is reasonably possible to make the same in color photographs of this type, an exemplary plant of 'AMIECH1604' grown in a commercial greenhouse in Heerhugowaard, the Netherlands. This plant is approximately 9 months old, shown planted in an 8.5 cm container.
Figure 2:
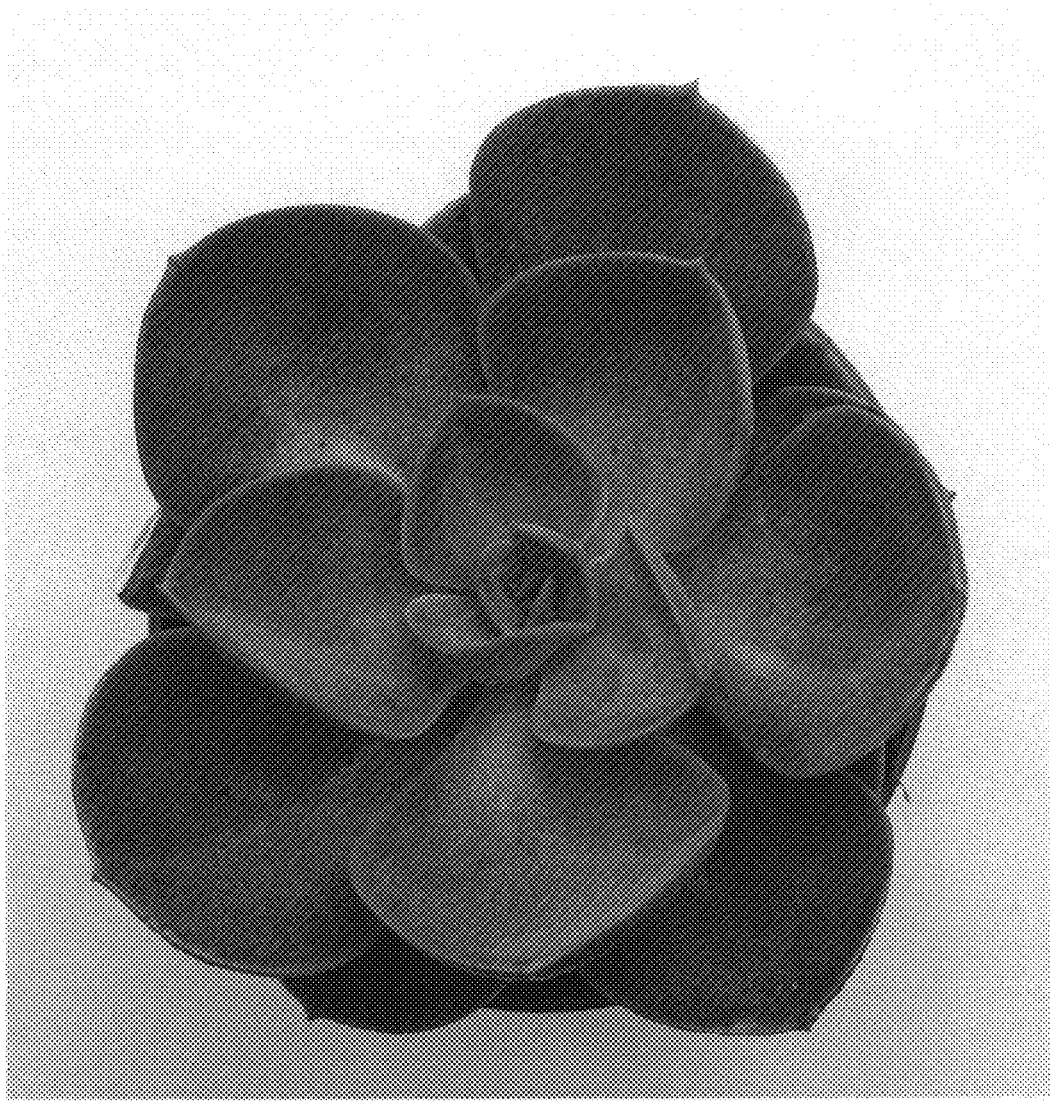
FIG. 2 illustrates, as nearly true as it is reasonably possible to make the same in color photographs of this type, the typical foliage arrangement of 'AMIECH1604'.
Figure 3:
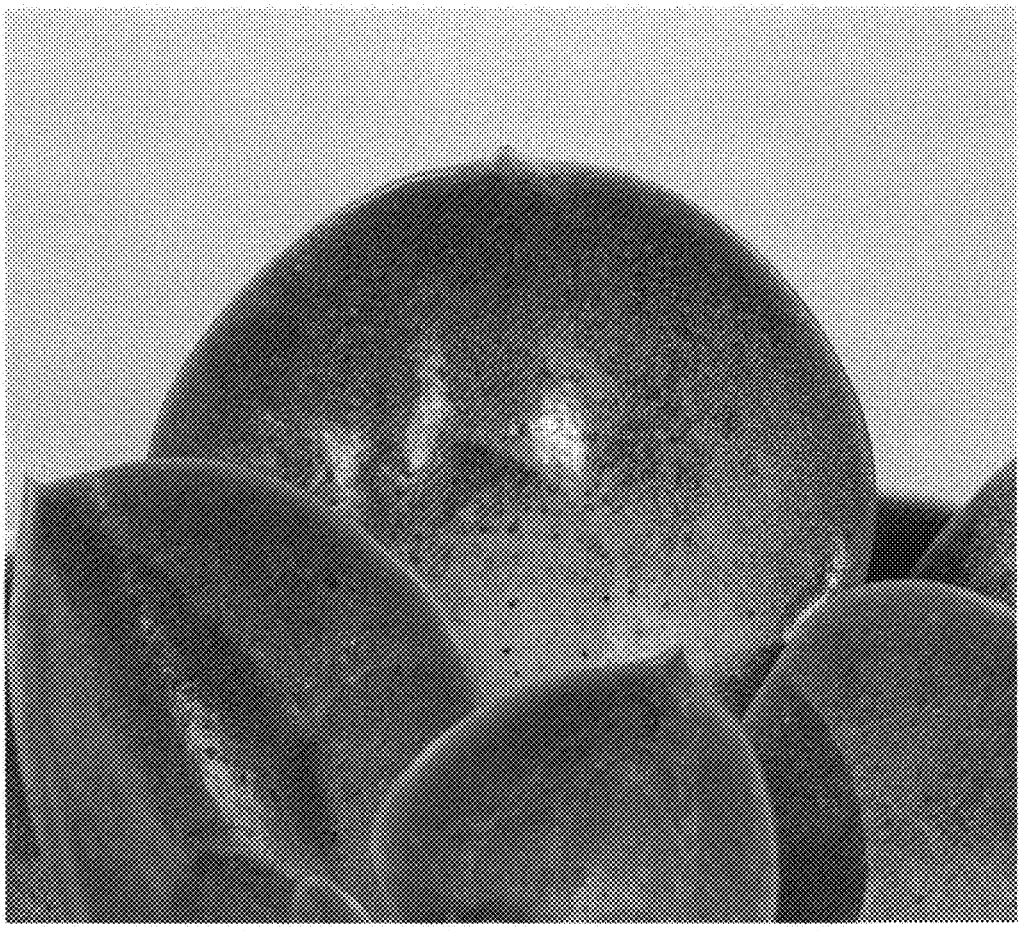
FIG. 3 illustrates, as nearly true as it is reasonably possible to make the same in color photographs of this type, the adaxial surface of the mature foliage 'AMIECH1604'.
Figure 4:
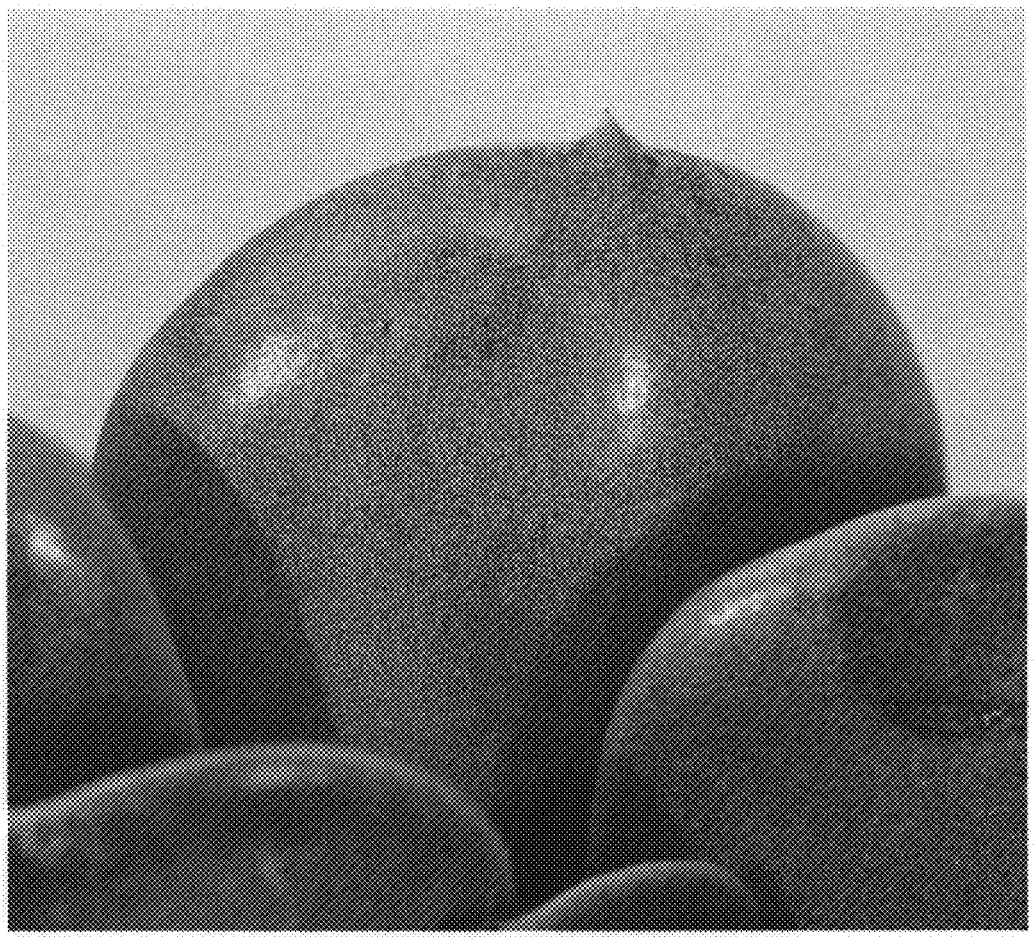
FIG. 4 illustrates, as nearly true as it is reasonably possible to make the same in color photographs of this type, the abaxial surface of the mature foliage 'AMIECH1604'.

The following observations and measurements made in November of 2016 describe averages from a sample set of six specimens of 9 months old 'AMIECH1604' plants grown in 8.5 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1604' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIECH1604' and a comparison with the parent and closest known comparator, *Echeveria* 'Perle Von Nürnberg', is provided below.

Plant description:

*Growth habit.*—Succulent perennial with foliage growing in a non-branched basal rosette.

*Plant shape.*—Flattened to flattened globular.

*Height from soil level to top of foliar plane.*—4.0 cm.

*Plant spread.*—Average of 11.0 cm.

*Growth rate.*—Fast.

*Plant vigor.*—Vigorous.

*Propagation.*—Type — Leaf cuttings. Time to initiate rooting — Approximately 15 to 30 days at an approximate temperature range of 18 to 25 degrees Celsius. Crop time — Approximately 20 to 30 weeks to produce a marketable plant in a 7 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

*Root system:*

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 21 leaves per rosette.

*Shape.*—Thick, succulent leaves which are broad obovate to short spatulate.

*Dimensions.*—5.5 cm long, 4.0 cm wide, and 0.5 cm thick, on average.

*Aspect.*—Slightly concave.

*Attitude.*—Very slightly curved upward.

*Apex.*—Short apiculate.

*Base.*—Cuneate.

*Margin.*—Entire; not undulated or lobed.

*Pubescence, texture and luster of the adaxial surface.*—Glabrous, smooth, and matte; moderately pruinose, colored grey, nearest to RHS 201D.

*Pubescence, texture and luster of the abaxial surface.*—Glabrous, smooth, and matte; moderately pruinose, colored grey, nearest to RHS 201D.

*Color.*—Juvenile foliage, adaxial surface — Greyed-purple, nearest to RHS 183A, and fading to red towards the base, in between RHS 54A and 54B; margins and apex are greyed-purple, nearest to RHS 185B. Juvenile foliage, abaxial surface — Greyed-purple, nearest to RHS 183B, and fading to red towards the base, in between RHS 54A and 54B; margins and apex are greyed-purple, nearest to RHS 185B. Mature foliage, adaxial surface — Greyed-green, nearest to RHS 197A yet darker, and suffused with yellow-green, RHS 152A; suffused with red towards the base, nearest to RHS 54B; margins are greyed-red, in between RHS 180B and 180C. Mature foliage, abaxial surface — Greyed-green, nearest to RHS 197A, and lightly suffused with yellow-green, RHS 152A; suffused with red towards the base, nearest to RHS 54C; margins are greyed-red, in between RHS 180A and 180B.

*Venation.*—Pattern — No venation is visible on the adaxial surface and only one main vein is visible on the abaxial surface. Color, adaxial surface — No venation is visible. Color, abaxial surface — Greyed-purple, RHS 184C.

*Petiole.*—No petiole; leaves are sessile.

Inflorescence: No flowering has been observed to date.

Comparisons with the parent plant and closest known comparator: Plants of the new cultivar 'AMIECH1604' differ from the parent, *Echeveria* 'Perle Von Nürnberg', which is also the closest known comparator, in the following characteristics described in Table 1 below.

TABLE 1

| Characteristic | 'AMIECH1604' | 'Perle Von Nürnberg' |
|---|---|---|
| Winter hardiness. | More hardy than the parent. | Less hardy than 'AMIECH1604'. |
| General coloration of the juvenile foliage. | Pink to red. | Soft red-purple. |
| General coloration of the mature foliage. | Red-purple. | Soft greyed-purple. |
| Leaf thickness. | Thicker and more robust. | Thin and weak. |

That which is claimed is:

1. A new and distinct variety of *Echeveria* plant named 'AMIECH1604', substantially as described and illustrated herein.

* * * * *